United States Patent
O'Keefe

(10) Patent No.: US 6,453,185 B1
(45) Date of Patent: Sep. 17, 2002

(54) VENTRICULAR CATHETER WITH REDUCED SIZE CONNECTOR AND METHOD OF USE

(75) Inventor: Jonathan B. O'Keefe, Coronado, CA (US)

(73) Assignee: Integra LifeSciences, Inc., Plainsboro, NJ (US)

( * ) Notice: Subject to any disclaimer, the term of this patent is extended or adjusted under 35 U.S.C. 154(b) by 0 days.

(21) Appl. No.: 09/528,478

(22) Filed: Mar. 17, 2000

(51) Int. Cl.$^7$ ................................................. A61B 5/04
(52) U.S. Cl. ........................ 600/378; 600/383; 600/561; 606/129
(58) Field of Search ............................... 606/129, 130; 600/544, 378, 383, 561; 128/898

(56) References Cited

U.S. PATENT DOCUMENTS

| | | | |
|---|---|---|---|
| 5,312,357 A | 5/1994 | Buijs et al. | 604/164 |
| 5,390,268 A | 2/1995 | Morlion et al. | 385/59 |
| 5,892,870 A | 4/1999 | Fingler et al. | 385/59 |
| 5,957,912 A * | 9/1999 | Heitzmann | 600/561 |
| 6,193,691 B1 * | 2/2001 | Beards et al. | 604/164.01 |
| 6,210,346 B1 * | 4/2001 | Hall et al. | 600/501 |

* cited by examiner

*Primary Examiner*—Linda C. M. Dvorak
*Assistant Examiner*—David M. Ruddy
(74) *Attorney, Agent, or Firm*—Fulwider Patton Lee & Utecht, LLP

(57) ABSTRACT

A sensing and drainage catheter for use in a cranial site includes a reduced diameter connector so that traditional tunneling techniques may be used with the connector-equipped proximal end of the catheter, rather than the sensor-equipped distal end of the catheter. The catheter includes a drainage lumen and a signal conducting lumen. The signal conducting lumen including a distal sensor for sensing the properties of cerebral spinal fluid and means for transmitting data signals representing those properties in either optical or electrical form to a reduced diameter connector attached to the proximal end of the lumen. A method comprises first accurately locating the distal end of the ventricular catheter in the brain ventricle prior to the catheter being tunneled under the scalp. The connector end of the catheter is then tunneled or threaded through a subdermal tunnel, and is then coupled to a counterpart connector for communication of the sensor signals to a monitor, and the drainage lumen is coupled to a bag for receiving excess CSF.

44 Claims, 8 Drawing Sheets

VENTRICULAR CATHETER WITH REDUCED SIZE CONNECTOR AND METHOD OF USE

BACKGROUND

The invention generally relates to an improved catheter and a method for treating conditions of the brain area and, more particularly, to an improved ventricular catheter adapted for placement in a subdermal tunnel, and a method for sensing physical parameters in the skull area with a ventricular catheter and placing the catheter in a subdermal tunnel in an improved manner to expedite the subdermal placement procedure and to reduce the risk of infection.

Head injuries, other pathologic neurological disorders and systemic diseases have been shown to cause acute swelling of the brain or an increase in the volume of cerebral spinal fluid ("CSF"). The so-called "closed-box" cranial vault restricts the amount of increase that can be tolerated before the increase in intracranial pressure poses a danger to the patient. The contents of the cranial vault are essentially non-compressible and comprise approximately 80% brain, 10% CSF and 10% blood. An increase in one of the components requires a decrease in one or both of the others to accommodate the change. An increase in the brain or CSF may result in undue pressure on healthy tissue resulting in temporary or permanent disability to the patient. Intracranial pressure sensors, catheters and shunts have been developed to monitor and manage the treatment of these patients, either through the recording and manipulation of information from the sensor or through the shunting mechanism from a catheter in the ventricle.

The intracranial pressure monitoring devices are introduced into the brain through an access hole in the skull. When placement in the ventricle is desired, the opening is appropriately close to the anterior horn of the lateral ventricle and the catheter and/or sensor is inserted through the access hole into the ventricular space. The pressure sensor in the distal end of the catheter conducts information via a cable in the catheter to an external monitor. Simultaneously, fluid may be drained from the ventricle and collected in an external drainage bag or system to relieve pressure. The monitoring and management of the patient may be hours or many days, typically five to ten days.

Because of the extended amount of time that the ventricular catheter must be positioned in the patient, and because of the invasive nature of the procedure, another consideration is the increased risk of infection of brain tissue by pathogens entering through the skull opening or access hole. The presence of a direct pathway through the skull access hole from an outside environment directly into the brain ventricle causes a substantial risk of infection. To reduce this risk, a catheter placement technique referred to as subdermal tunneling has been developed.

In the prior fluid-filled pressure sensing catheter approach, a foil strain gauge or rosette of strain gauges is located at the proximal end of the catheter or within an apparatus outside of the catheter. The distal end of the catheter is inserted into the cranium and receives fluid from the cranium in a lumen extending completely through the catheter to the proximal end. The fluid pressure in the catheter lumen acts on the surface to which the gauges are attached and the gauge or gauges provide an electrical signal representative of the strain in the surface which can be correlated to pressure in the cranium.

In this fluid-filled catheter approach, traditional or forward tunneling under the scalp is typically used. A surgeon makes an incision, or first opening, in the patient's scalp exposing a portion of the skull overlying a ventricle of the brain. Subsequently, a twist drill access hole is formed through the skull exposing the interior of the cranial vault. Next, the distal end of the fluid-filled catheter is inserted into the twist drill access hole after which the proximal end of the catheter is connected to a sharp pointed tunneling instrument, such as a trocar or needle. The trocar is inserted under the scalp at the point of incision just proximal of the skull access hole and is advanced through the scalp to form a subdermal tunnel of typically five or more centimeters. The tunneling instrument is pulled through the tunnel to exit the scalp at this exit opening. The proximal end of the catheter, which is attached to the end of the trocar, is also pulled through the tunnel and is then pulled taut in the tunnel. The surgeon then sutures the scalp over the skull access hole and over the tunnel entrance and exit thereby sealing the skull access hole and the scalp openings.

The diameter of the tunnel is kept as small as possible and is just larger than the diameter of the catheter that must be threaded through the tunnel. The small diameter of the tunnel contributes to lowering the risk of infection. It has been found that the subdermal tunnel technique substantially decreases the risk of intracranial infection by providing an elongate tunnel through which pathogenic organisms would have to pass before they could enter the cranial vault through the skull access hole. There is thus no direct pathway for contamination to enter the access hole. The tunneling technique has proven very successful.

One of the drawbacks of a fluid filled catheter is that the pressure head created by the fluid column in the catheter must be subtracted from the pressure readings to get an estimate of the actual CSF pressure within the brain ventricle. The common use of oscillating beds in head injury cases further complicates this problem by causing fluctuations in the fluid column. To solve the pressure measurement problem associated with fluid filled catheters, transducer tipped catheters that include sensors, typically strain gauges or optical sensors, placed within the catheter's distal end were developed.

Transducer tipped catheters used in ventricle pressure sensing have a transducer of an electrical or optical nature located at the distal tip of the catheter, that is placed within the cranium of the patient. There is an elongate shaft connecting the catheter's distal end with its proximal end. The proximal end of the catheter includes a connector that is used to connect the internal optical or electrical conductors to another connector located on an intermediary cable or directly on an instrument for displaying the pressure sensed or other physical parameter that has been sensed to the physician and nursing staff. Such connectors not only interconnect the signal communication line, but also provide a physical device that locks the two connectors together to apply the necessary pressure to force the internal conductor of one connector into good signal contact with the internal conductor of the other connector, and so that they do not become inadvertently disconnected. Because of this locking device and other design parameters of prior connectors, they have been too large to fit within the small subdermal tunnel discussed above. Therefore, transducer tipped catheters have been reverse tunneled.

Reverse tunneling is similar to traditional tunneling except that the trocar is used to puncture the scalp at a location distal of the skull access hole and is tunneled towards the skull access hole from the distal location. After formation of the subdermal tunnel, the distal end of the catheter, which is smaller than the connector, is inserted into the second scalp opening (remote from the skull access hole) and pulled through the tunnel to the scalp opening adjacent the skull access hole. The needed length of catheter is pulled through the tunnel in the direction of the skull access hole up to the point that the large connector or other device mounted to the catheter cannot be pulled farther. The large connector will either come into contact with the distal scalp opening or, if partially pulled into the tunnel, will be prevented from further advancement due to its larger size as compared to the smaller diameter of the tunnel. The physician then positions the distal end of the catheter in the ventricle or other cranial location as desired and the catheter is fixed in the desired in-dwelling position in the skull access hole. The excess catheter length is then pulled in the opposite direction through the tunnel in the direction of the distal scalp opening to make the catheter shaft taut, and the suturing of the scalp over the access hole and the tunnel openings may then occur.

An example of such a transducer tipped catheter and the above-described technique of tunneling is shown in U.S. Pat. No. 5,312,357 to Buijs et al. FIGS. 2a through 2f in general show the prior method described above. FIGS. 8a through 8h also show the prior method described in addition to showing the typically large proximal end connector of such catheters.

Although the use of ventricular catheters having a sensor or sensors located at their distal tips is advantageous in that such catheters provide direct readings of pressure or other physical parameters in the cranial area, the reverse tunneling technique required to use such catheters is disadvantageous in that the distal end of the sensor equipped catheter must pass through the subdermal tunnel thereby exposing the distal tip to possible contamination with foreign matter, pathogens, or other infectious agents. Any pathogens that may be introduced into the brain through the skull access hole may create a subcranial infection with severe adverse consequences for the patient. Thus, great care must be taken with this prior tunneling method and as a result, it is substantially less desirable than the traditional tunneling method.

In addition, the above-described reverse tunneling method has been found to make it more difficult in many cases to locate the distal tip of the ventricular catheter in the proper position in the ventricle of the patient. When the shaft of the catheter is already located in the subdermal tunnel, the remainder of the catheter shaft between the tunnel and the distal tip is restrained in its movement due to the proximal end being located in the tunnel. Even though the catheter has been threaded through the tunnel to provide as much slack as possible for the distal end of the catheter, the fact that the proximal end of the catheter is held firmly in a fixed position can act as a restraint on the physician's ability to maneuver the distal tip of the ventricular catheter during its placement in the patient's ventricle. As is well known to those skilled in the art, it takes a large amount of skill under the best circumstances to accurately place the ventricular catheter in the correct position in the patient's ventricle without causing excessive trauma to the patient. The added problem of having to deal with a restrained proximal end of the ventricular catheter requires an even greater level of skill. The large size of the connector at the proximal end of the ventricular catheter has made the above problems occur. Increasing the tunnel size so that the proximal end connector could itself be pulled through the tunnel would defeat the antiinfection purpose of the tunnel.

Furthermore, the above-described tunneling technique occurs before placement of the distal end of the catheter in the patient's cranium, thus delaying the stabilization of the patient. Using two catheters, one to first stabilize the patient while the second more permanent catheter is being tunneled, is undesirable due to exposing the patient to the increased trauma of two catheters and two access holes. It would be preferable to be able to immediately relieve excess pressure on the patient's brain with the same catheter that will be tunneled in the subdermal tunnel for location of the catheter shaft and thus lower the trauma to the patient.

Another area in which improvement is desired is in the process of threading the catheter through the subdermal tunnel. In some cases, needle-type devices are used to form the tunnel and as a result, tissue and blood are encountered by either the proximal end or the distal end of the ventricular catheter depending upon whether the catheter is traditionally or reverse tunneled. It would be desirable to insulate the ventricular catheter from these possible contaminants as much as possible. Further, any device used in the tunneling should assist in threading the catheter through the tunnel so that the catheter is not crimped, stretched, or kinked in any way. As is well known, crimping, stretching, or kinking can damage internal components of the catheter, such as optical fibers or electrical conductors, making the catheter inaccurate or unusable. Various approaches at solving these concerns have been attempted, including a notch formed in a guide type device located in the tunnel and in which the catheter is threaded. However, the notch is open and may accumulate contaminants.

Hence those skilled in the art have recognized a need for a catheter having a sensor or sensors located at its distal end, and that is small enough so that it may be placed in a subdermal tunnel but need not be first located in the tunnel prior to location in the patient's cranium. In addition, a catheter that can be tunneled in this way and that is able to both measure a biological parameter or parameters within the cranium and provide for drainage of CSF when required, and having a small outer diameter for reduced trauma to the patient is needed. Further, it is desirable that such a catheter be able to accept a stylet for use in placing the catheter in the correct position in the cranium, yet provide means to protect the internal lumen or lumina of the catheter when exposed to the threading process through the tunnel. A need has also been recognized for a catheter and method whereby a single catheter may be used for immediately stabilizing the patient and may also be used for long term use, thereby obviating the need for two catheters and for two access holes. Further, a need has been recognized for a method of placing the catheter in the cranium of the patient first so that the patient may be stabilized as soon as possible, and then providing a tunneling step for more long term location of the catheter shaft in a subdermal location. The present invention satisfies these needs and others.

SUMMARY OF THE INVENTION

The present invention provides a catheter having proximal and distal ends, including a drainage lumen and a distal sensor for sensing a selected physical property or properties in the cranium of a patient and for transmitting signals representing those properties in either optical or electrical form to a miniaturized proximal connector at the catheter's proximal end. The miniaturized connector is configured to have a size such that it can be pulled through a subdermal tunnel by a tunneling instrument so that a traditional or forward tunneling technique may be used with the sensor-tipped catheter. A skull access hole that provides access to a ventricle of a patient's brain is formed, the catheter inserted in the access hole by the physician, and then the adjacent subdermal tunnel is formed. The proximal end of the catheter is then pulled through the subdermal tunnel while the distal end of the catheter remains in position in the access hole.

In another aspect, the drainage lumen of the catheter includes multiple ports in the distal end for receipt of CSF and includes a drain port in the proximal end for drainage to a collection apparatus. The drain port and lumen also serve to receive a stylet for use in stiffening the catheter for initial insertion of the distal end of the catheter through the access hole and into the ventricle of the patient. The drainage/stylet lumen is terminated in the intermediate portion of the catheter body so that fluid must leave the lumen through the drainage/stylet port. This prevents fluid internal to the catheter from reaching the proximal end of the catheter where the miniaturized connector is located.

Generally, the present invention contemplates a method for placement of a catheter in a patient by first placing the catheter through an access hole created in the cranium, locating the catheter in a desired position within a ventricle of the brain, and then securing the external part of the catheter shaft within a subdermal tunnel in the patient's scalp. In more detailed aspects, such a catheter may be used in measuring intracranial fluid characteristics by forming an incision exposing a region of the skull over a ventricle of the brain; creating a twist drill access hole through the skull having fluid pressure; placing the distal sensor-equipped end of the catheter into the twist drill access hole; attaching the proximal end of the catheter to a tunneling instrument; using the tunneling instrument to form a subdermal tunnel from the twist drill access hole to a point distal of the access hole, and forming a second opening with the tunneling instrument at the distal location; removing the tunneling instrument through the second opening and pulling the attached catheter taut through the second opening; connecting the drainage lumen to a fluid collection apparatus; and connecting the miniaturized connecter mounted at the proximal end of the catheter to an intermediate connector and thereby sensing CSF characteristics transmitted from the sensor equipped catheter.

Thus the method and apparatus of the present invention provide a catheter having a sensor located at the distal tip of the catheter, having a drainage lumen, and a miniaturized connector at the proximal end of the catheter that allows the catheter to be forwardly tunneled, thereby eliminating the possibility of distal tip contamination that may occur with reverse tunneling techniques. The miniaturized connector also removes a restraint on the physician's ability to properly locate the catheter in the patient in that the proximal end of the catheter is not placed in the tunnel prior to placement of the distal tip in the ventricle of the patient. In addition, the catheter of the present invention uses a single opening which serves to receive a stylet for placement of the catheter and as a drain port thereafter.

Direct placement of the distal end of the catheter in the skull access hole without the need to first thread it through a subdermal tunnel in accordance with aspects of the invention eliminates the possibility of contaminating the distal end with foreign matter or infectious agents, the primary weakness of the prior art, and permits the physician to accurately position the catheter in the patient without having the restraint of the proximal end of the catheter already located in the subdermal tunnel, also a weakness of the prior art.

Other features and advantages of the invention will become more apparent from the following detailed description of preferred embodiments of the invention, when taken in conjunction with the accompanying exemplary drawings.

DETAILED DESCRIPTION OF THE PREFERRED EMBODIMENTS

Figure 1:
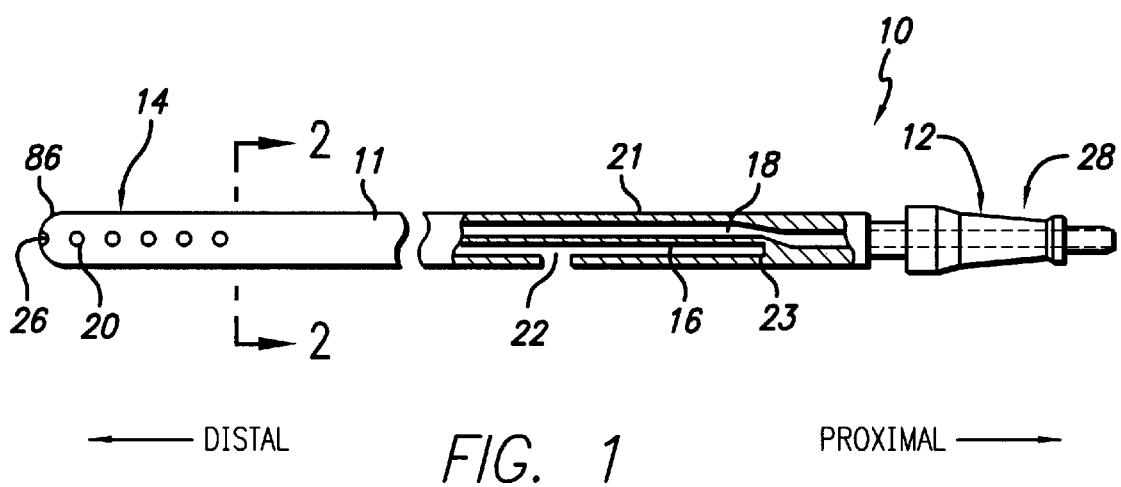
FIG. 1 is a partial cut-away view of an intracranial catheter in accordance with aspects of the present invention showing an optical pressure sensor and drainage holes at the distal end, a drainage/stylet port formed along the intermediate portion of the catheter shaft, a drainage/stylet lumen that terminates in the intermediate portion of the catheter shaft, and a reduced diameter connector at the proximal end of the catheter shaft.

In the following description, like reference numerals are used to refer to like or corresponding elements in the different figures of the drawings. Referring now to the drawings with more particularity, in FIGS. 1 and 2 there is shown a catheter 10 that generally comprises an elongate flexible body 11 having a proximal end 12 and a distal end 14 with a drainage/stylet lumen 16 and a signal conducting lumen 18 located therebetween. The drainage/stylet lumen 16 includes near the distal end 14 rows of drainage apertures 20 that conduct fluid from the outer surface of the catheter body 11 to the drainage/stylet lumen 16, thereby placing the lumen 16 in fluid communication with CSF when the distal end 14 of the catheter 10 is placed within a ventricular cavity. The intermediate portion 21 of the catheter body 11 also includes a drainage/stylet port 22 in communication with the drainage/stylet lumen 16. The drainage/stylet port 22 and drainage/stylet lumen 16 may receive a stylet 24 such as that shown in FIG. 3, that aids in insertion of the distal end 14 of the catheter 10 within a ventricular cavity, as is discussed in relation to FIG. 13 below in more detail. The port 22 is located in the intermediate portion 21 of the catheter body 11 between the distal end 14 and the proximal end 12 at a location spaced from the distal end 14 such that the distance between the distal end and the port 22 is less than the length of the stylet.

The drainage/stylet lumen 16 terminates within the catheter body 11 at a location 23 proximal to the port 22 as shown in FIG. 1 but distal to the proximal end 12. At that point the lumen is closed 23. Therefore, the only access to the lumen 16 is through the drainage apertures 20 at the distal end and the drainage/stylet port 22 located in the intermediate portion of the catheter body 11. Because the drainage/stylet lumen 16 terminates before the proximal end of the catheter 12, fluid received by the drainage holes 20 will not be in the vicinity of the proximal end 12 of the catheter 10 where the signal connector is attached. This lessens the possibility that CSF or other fluid will contaminate the connector.

After the installation of the catheter 10 in the ventricle and after it has been placed in the scalp tunnel, as discussed in more detail below, the drainage/stylet port 22 may be fitted with a fluid connector to facilitate coupling the drainage lumen 16 to a separate fluid collection vessel or apparatus, such as a bag. In this manner, CSF may be drawn in the proximal direction through the drainage apertures 20, through the drainage/stylet lumen 16, and out of the fluid connector at the drainage/stylet port 22.

Figure 4:
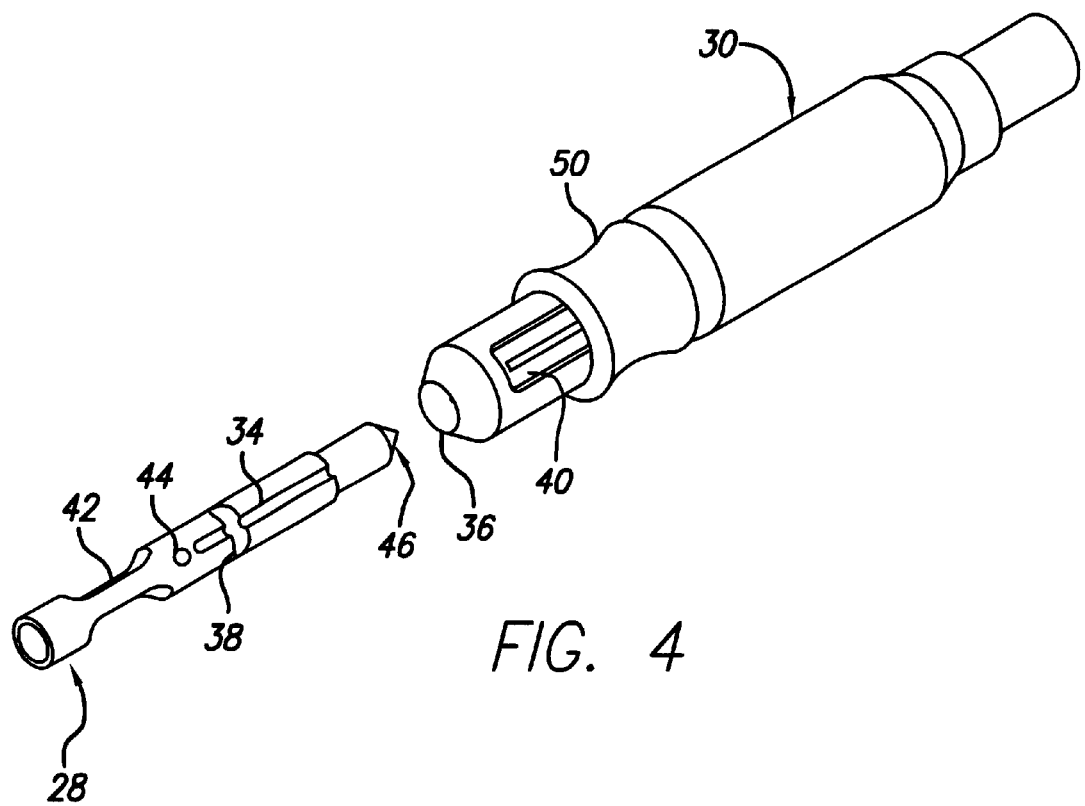
FIG. 4 is an enlarged perspective view of a reduced diameter male connector and a mating female connector embodying features of the present invention, the male connector being the connector shown at the proximal end of the catheter in FIG. 1, and the mating female connector being mounted on an intermediate cable or instrument, for example.

The signal conducting lumen 18 in this embodiment houses a pressure sensing and transmitting apparatus 26, that is operative to sense pressure at a location within the cranial cavity. In this embodiment, the apparatus comprises an optical pressure sensor 26. Connected to the pressure sensor 26 is an optical fiber (not shown) that is disposed in the signal conducting lumen 18 such that data signals from the sensor 26 are transmitted by the optical fiber through the lumen 18 to a miniaturized male connector 28 that is attached to the proximal end 12 of the catheter body 11. The signal conducting lumen 18 may include a fiber optic cable for the transmission of data signals in the form of modulated light from the pressure sensor 26 to the male connector 28 as mentioned above or the lumen 18 may include an electrical conductor for the transmission of modulated electrical signals from the sensor 26 to the male connector 28, depending on the sensor used or the lumen may house both electrical and optical conductors. The reduced diameter or miniaturized male connector 28 may be connected to a mating female connector 30 as shown in FIG. 4 for connection to an external pressure monitor or other device operative to provide a discernable pressure reading.

Figure 2:
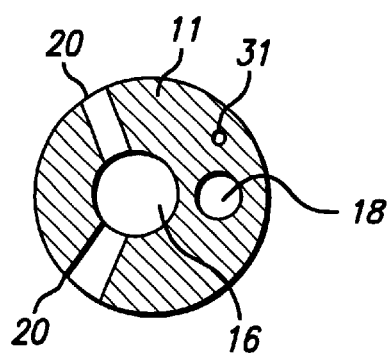
FIG. 2 is a cross sectional view through lines 2—2 of FIG. 1, showing the lumina structure of the catheter of this embodiment and in particular, demonstrating a configuration where radial drainage holes spaced approximately 160 degrees apart in the body of the catheter are interconnected by the drainage/stylet lumen, also showing a second lumen used for optical fibers or electrical conductors, depending on the type of pressure sensor used at the distal end of the catheter, and also showing a tensile member.
Figure 3:
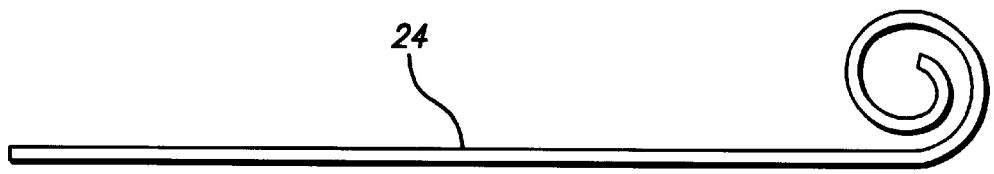
FIG. 3 is a side elevational view of a stylet member useable in conjunction with the intra-cranial catheter of FIG. 1, wherein the stylet would be positioned in the drainage/stylet port shown in FIG. 1 to assist the physician in properly locating the catheter in the ventricle.

Referring in particular to FIG. 2, the catheter 10 of this embodiment also includes a tensile member 31. In an optical embodiment of the catheter 10, that is, where the catheter contains an optical fiber or fibers, the fragility of the optical fibers that reside in the signal conducting lumen 18 may make it desirable to include a tensile member 31, such as a wire, within the body 11 of the catheter to prevent the optical fiber from becoming stretched in a manner that could result in its breakage. However, the tensile member 31 may not be included in embodiments of the device wherein the pressure sensor 26 and the signal conductor are other than optical, e.g., electric. The tensile member is formed of a biocompatible material such as stainless steel, an aramid such as Kevlar®, MP 35N, a shape memory material, or other materials that exhibit any or all of the characteristics of being radiopaque, imageable, non-ferro-magnetic, flexible, and having high tensile strength. In one embodiment, the tensile member is coextruded into the wall of the catheter as the catheter body 11 is manufactured.

In the case where no tensile member is used, such as in the case where electrical conductors are used in the catheter body, markers may be placed in the catheter body. These markers are radiopaque to assist in locating the catheter in the patient. Various marker arrangements may be used, such as a longitudinal stripe coextruded in the catheter body wall along the entire length of the catheter. In another, marker bands may be embedded in the distal region of the catheter. In yet another arrangement, filler material such as barium sulfate, may be inserted in the distal tip of the catheter. Markers may also be printed on the catheter distal region or elsewhere.

Also shown in FIG. 2 are two drainage holes 20. Considering FIGS. 1 and 2 together, in this embodiment, there is an array of drainage holes comprising two rows which are spaced apart by an arc of approximately 160°. The separation may vary however, and more or fewer rows or other arrangements of drainage holes may be used.

Figure 5:
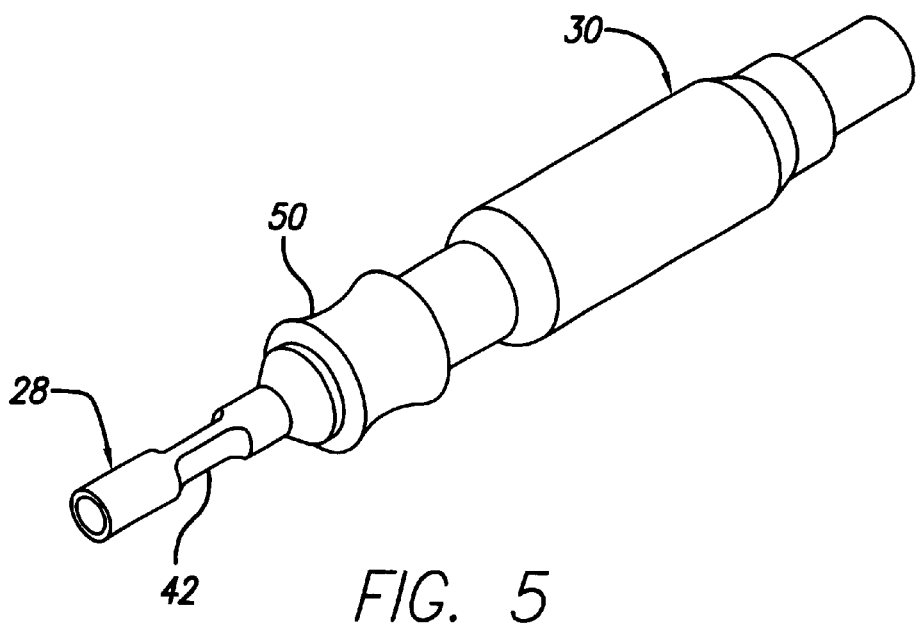
FIG. 5 is an enlarged perspective showing the male and female connectors of FIG. 4 joined together so that optical or electrical signals, or both, are efficiently communicated from the sensor of the catheter, as shown in FIG. 1, to the proximal end of a cable or other device of which the female connector forms a part.

Referring now in more detail to FIGS. 4 and 5, the miniaturized, or reduced diameter male connector 28 is shown. This male connector 28 is also shown in FIG. 1 and includes an outer cylindrical engagement body 32, and a guide tip 46. The engagement body 32 is dimensioned such that it is the same size or is smaller than the diameter of a subdermal tunnel through which it is to be threaded (shown in FIG. 15 and discussed below). In a particularly preferred embodiment, the engagement body 32 is dimensioned to be slidably received within a subdermal tunnel having a diameter of less than about 10 French and preferably 5 to 9 French.

The engagement body 32 of this embodiment further includes an alignment groove 34 that slidably engages an alignment boss 36 located on an internal surface of the female connector 30. The alignment groove 34 and alignment boss 36 assist in aligning the two connectors 28 and 30 as they are connected together and eliminate the possibility of connector misalignment. In another embodiment, alignment devices such as the groove 34 and boss 36 may not be necessary and no particular alignment may be required. The engagement body 32 also includes a locking groove 38 that is engaged by a locking finger 40 disposed on the female connector. In addition, a pair of finger grips 42 and an alignment marker 44 are provided for ease in manipulating the male connector 28 into the mating female connector 30. The male connector 28 is fully seated within the female connector 30 when the locking finger 40 engages the locking groove 38. The embodiment shown in FIGS. 4 and 5 includes a sliding lock ring 50. Once the locking groove 38 has engaged the locking finger 40, a sliding lock ring 50 on the female connector 40 is slid forward over the locking finger 40 and thereby prevents inadvertent disengagement of the connecters 28 and 30.

The alignment marker 44 may comprise a raised bump, a depression, a color indication, or other visual or tactile indicator. The alignment marker 44 will assist in more rapidly locating the alignment groove 34 into the boss 36.

The male and female connectors 28 and 30 may be adapted to transmit either optical data signals or electrical data signals or both electrical and optical signals depending on the sensor 26 and other device or devices used in the catheter. In the fiber optic embodiment, the connectors 28 and 30 both contain optical fibers and the connectors are keyed to each other such that the optical fiber ends will have abutting frusto-conical surfaces formed at the appropriate angle to each other in accordance with manufacturer's specifications. However, in another embodiment, such as where the ends of the optical fibers are spherical in shape, no particular relative alignment of the male and female connectors may be required. However, if electrical contacts exist, a particular alignment will likely be necessary.

Figure 6:
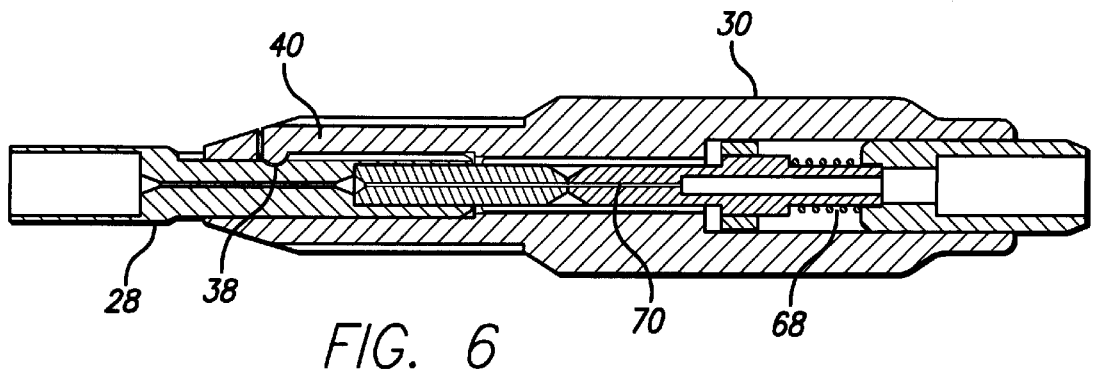
FIG. 6 is an enlarged sectional view of FIG. 5 showing the interconnection of the optical fibers of the joined male and female connectors so that optical signals are efficiently communicated from the sensor of the catheter, as shown in FIG. 1, to the proximal end of a cable or other device of which the female connector forms a part.

Referring to FIGS. 6 through 9, various connector embodiments are shown. FIG. 6 presents a cross-sectional view of FIG. 5. In FIG. 6, a male connector 28 is shown interconnected with a female connector 30. The female connector 30 includes the locking finger 40, which is a locking device, that has engaged the locking groove 38 formed in the male connector 28. As is apparent from the side view of this figure, the male connector 28 has been miniaturized and is much smaller in diameter than the female connector 30. The outer portion of a locking device, in this case the locking finger 40, is located on the female connector 30 while inner portion of a complementary locking device, in this case a recess or groove 38, is located on the male connector 28. This arrangement contributes to maintaining the male connector with a reduced diameter. The spring loading 68 of the optical fiber 70 and any other devices that may increase a connector size are included in the female connector 30. This approach permits the smallest size male connector possible so that the male connector 60 may be pulled through a subdermal tunnel.

The embodiment of FIG. 6 does not include the sliding locking ring 50 shown in FIGS. 4 and 5 as it was found to not be necessary in this embodiment. If it were needed, it is likely that it would be located on the female connector 30 as in the embodiments of FIGS. 4 and 5 so as to keep the diameter of the male connector 28 at a reduced size.

Figure 7:
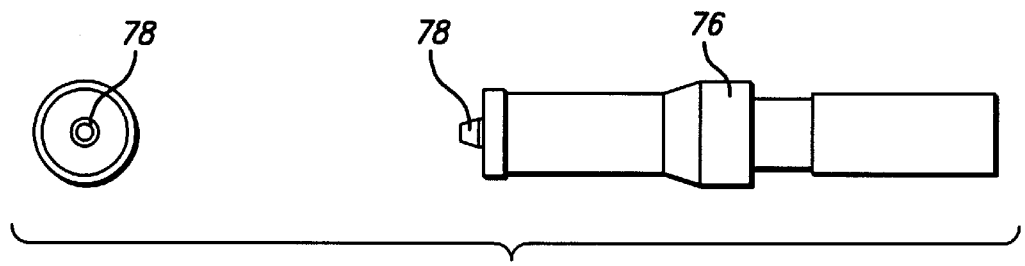
FIG. 7 comprises an enlarged profile view of an embodiment of a miniaturized male connector, for transmitting optical signals, embodying features of the present invention, and an end view of that connector.
Figure 8:
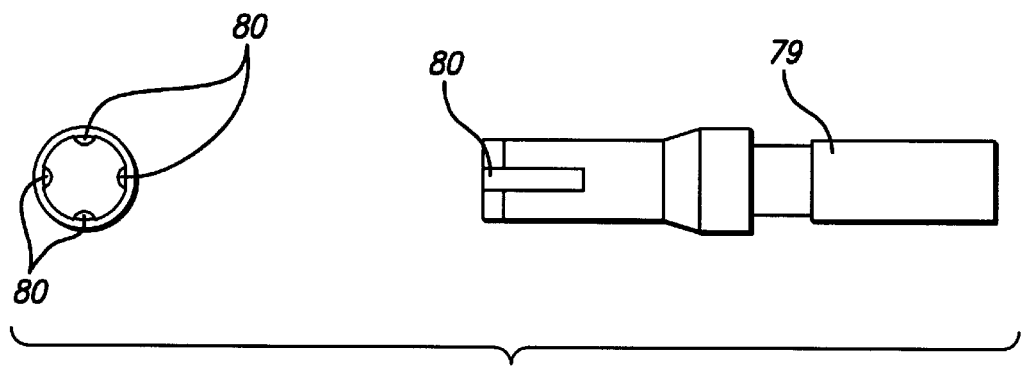
FIG. 8 is an enlarged profile view of an embodiment of a reduced size, miniaturized male connector, for transmitting electrical signals, embodying features of the present invention, and an end view of that connector.
Figure 9:
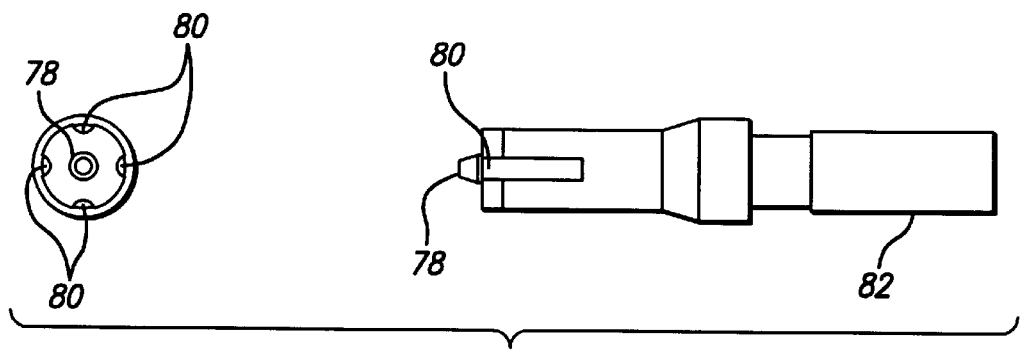
FIG. 9 is an enlarged profile view of an embodiment of a reduced size, miniaturized male connector, for transmitting both optical and electrical signals, embodying features of the present invention, and an end view of that connector.

Referring now to FIGS. 7, 8, and 9, different male connectors are shown. FIG. 7 presents an optical connector 76 with the optical fiber 78 located at the center of the connector, as in FIG. 6. FIG. 8 presents an electrical connector 79 with four electrical pads 80 located circumferentially around the connector mating surface. FIG. 9 shows a combination optical/electrical connector 82 having both an optical fiber 78 and electrical pads 80. Other arrangements of the electrical pads and optical fiber are possible.

Referring again to FIG. 1, typically, the pressure sensor 26 will be mounted within the signal conducting lumen 18, at the distal tip 86 of the catheter 10 so as to sense pressure at that location. Generally, when the pressure sensor 26 is located on the distal tip 86, the catheter 10 may be used to provide a reading of the CSF pressure or tissue pressure within a ventricle of the brain. The pressure sensor 26 may comprise a small optical-type pressure transducer. The choice of sensor 26 dictates the signal conducting means of the signal conducting lumen 18, i.e., either a fiber optic cable is used where an optical sensor is used or an electrical cable or cables are used in the case of an electrical sensor. In the optical embodiment, the proximal connector 28 will comprise an optical connector operative to connect the optical fiber that forms the signal conducting lumen 18 to an external pressure monitor or other device operable to receive optical indicia of pressure and to convert such optical indicia of pressure into discernable pressure readings.

Although shown as having two lumina in the figures herein; i.e., a drainage/stylet lumen 16 and a signal conducting lumen 18, fewer or more lumina may be used. For example, a single lumen may be used. In a single lumen case, a sensor located at the distal tip of the catheter may be used with the single lumen housing the conductor or conductors of the distal sensor that proceed to the proximal end of the catheter and the drainage holes would also communicate with that same lumen. In the case shown in the accompanying drawings, the tensile member 31 was located entirely within the catheter body wall during the coextrusion process. However, in the case of a tensile material that can not be coextruded, a tensile member lumen may be formed in the catheter and the tensile member threaded through that lumen. Such a tensile member can be anchored at the distal end of the catheter through the use of adhesive or other means.

Figure 10:
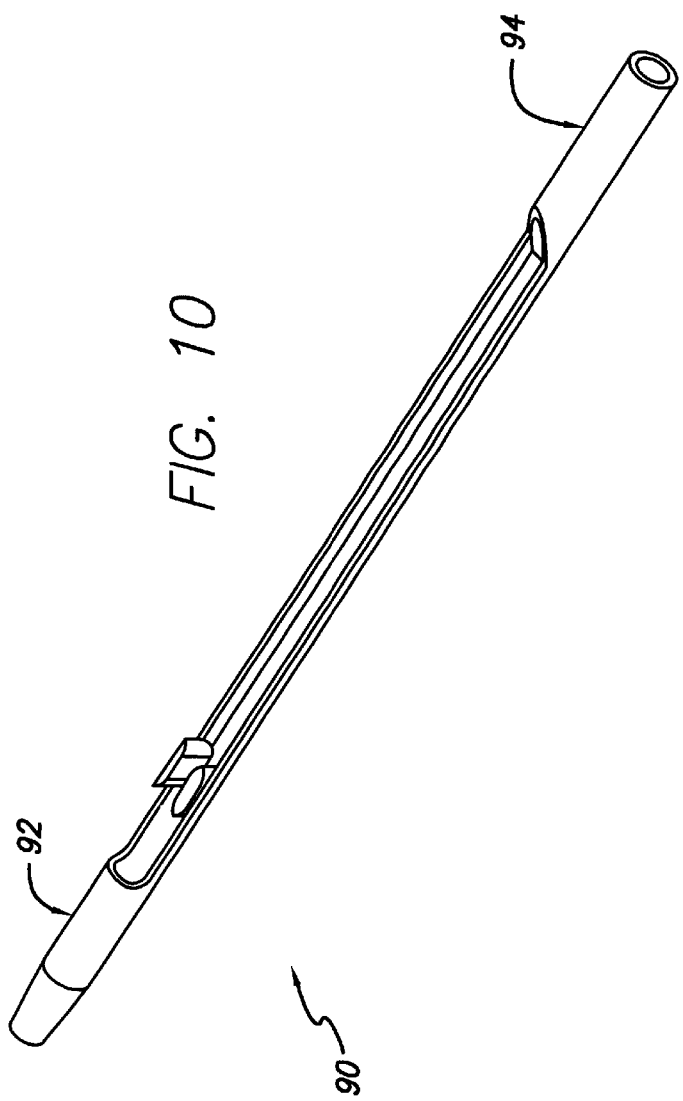
FIG. 10 is an enlarged perspective view of a protective tunneling sleeve in accordance with the present invention for protecting the miniaturized proximal connector and covering the drainage/stylet port during tunneling of the catheter.
Figure 11:
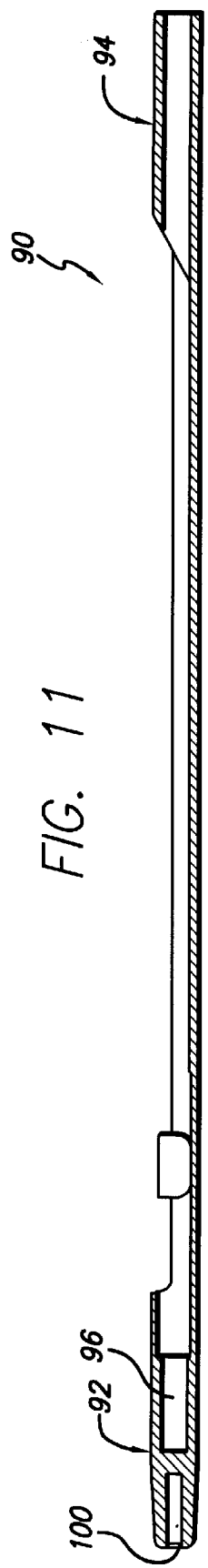
FIG. 11 is an enlarged sectional view of the protective tunneling sleeve of FIG. 10.
Figure 12:
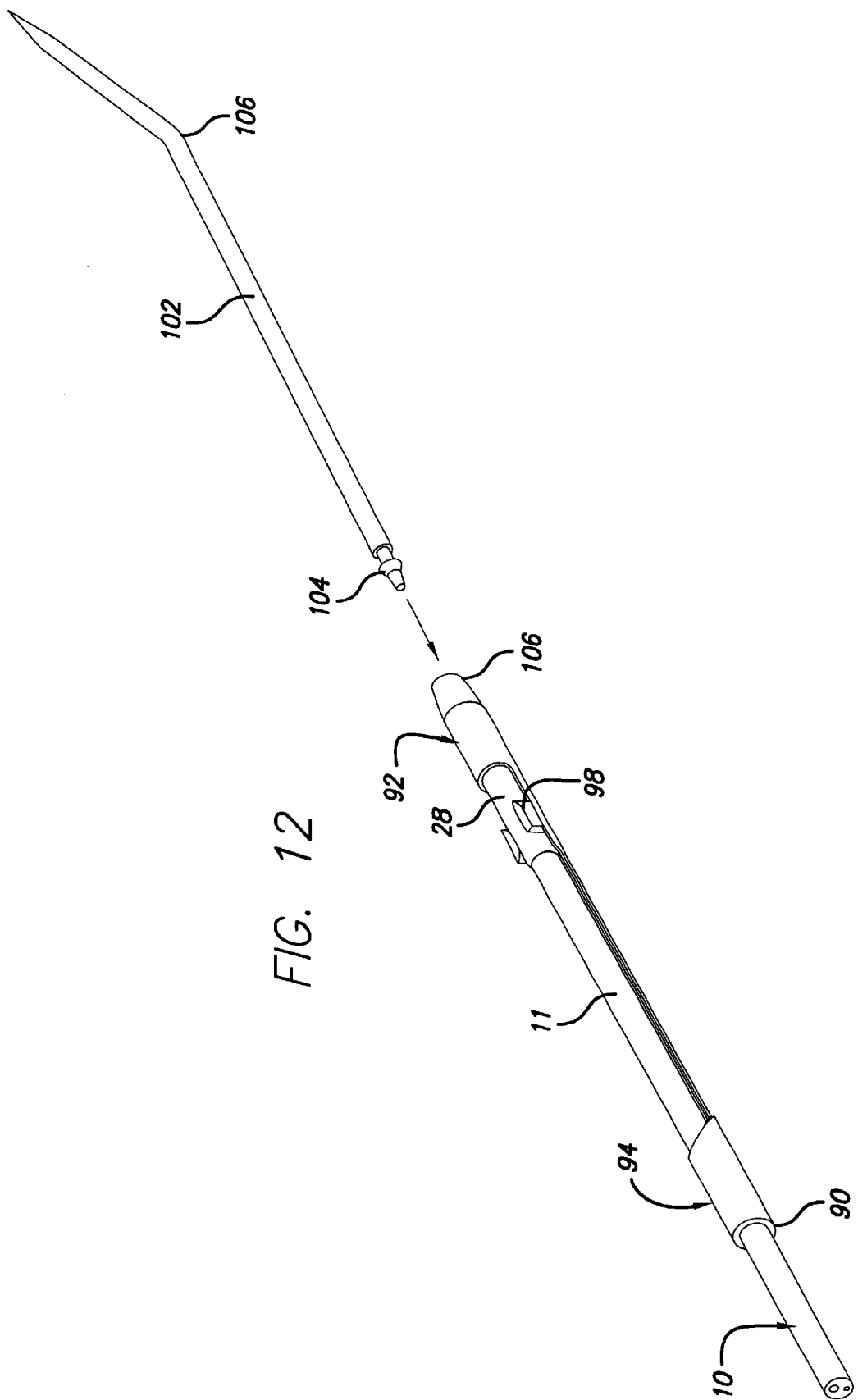
FIG. 12 is an enlarged perspective view of a tunneling instrument, in this case a solid trocar or needle, suitable for use in forming a subdermal tunnel in accordance with the method of the present invention, the trocar being shown in conjunction with the protective tunneling sleeve of FIG. 10.

Referring now to FIGS. 10, 11, and 12, a protective tunneling sleeve 90 is shown. The tunneling sleeve 90 comprises a proximal end 92 and a distal end 94. The proximal end is used to receive the male connector 28 of the catheter 10 and has a chamber that is completely closed 96 within which the connector resides during the time that it is pulled through the scalp tunnel, as will be described below in more detail. The sleeve 90 also includes a gripping device 98 taking the form of two opposed fingers that secure the sleeve on the catheter body 11, as shown in FIG. 12. The gripping fingers 98 are spaced apart by a distance that is less than the diameter of the catheter body 11 and thus secure the body 11 in relation to the sleeve 90.

The protective tunneling sleeve 90 also includes a drainage/stylet port cover section 94 comprising the entire distal end 94 of the sleeve. The port cover section protects the drainage/stylet port 22 as it is being drawn through a scalp tunnel so that contaminants do not enter the port 22. The distal section 94 of the protective tunneling sleeve 90 has an inner diameter that is larger than the diameter of the connector and catheter body so that the sleeve may be slid over the catheter body and into place. The sleeve 90 also includes a tunneling instrument opening 100 for receiving the barb or other connecting device of a tunneling instrument, such as a solid trocar, so that the sleeve 90 and its secured catheter 10, may be pulled through a scalp tunnel. Such a combination is shown in FIG. 12 where the solid trocar or needle 102 is shown with a proximal end barb 104 that is pressed into the instrument opening 100 of the sleeve 90. Although exaggerated for clarity of illustration in FIG. 12, the trocar may have a bend 106 of only approximately 5°.

As is apparent from reviewing FIG. 12, the diameter of the trocar 102 is less than the diameter of the protective tunneling sleeve 90 in this embodiment. Because the protective tunneling sleeve 90 fits over the miniaturized connector 28 located on the proximal end of the catheter, the miniaturized connector and catheter body 11 are smaller in diameter than the protective tunneling sleeve 90. Thus, when used to locate the catheter in a subdermal tunnel, as will be described in further detail below, the trocar is first advanced through the scalp to create a lead-in or pilot subdermal tunnel. Because the protective tunneling sleeve 90 is connected to the proximal end of the trocar, it is also pulled into the tunnel. The tapered end 106 of the protective tunneling sleeve 90 then operates to open the subdermal tunnel farther as the sleeve 90 is pulled through the trocar-created pilot tunnel. Thus, the miniaturized connector 28 is designed to be pulled through a subdermal tunnel and is, in this case, smaller than the diameter of the tunnel. There may be arrangements however in which the connector is the same size as the tunnel.

After the protective tunneling sleeve 90 and its secured catheter have been pulled through a scalp tunnel, the sleeve 90 may be removed from the catheter 10 by pulling it hard enough to overcome the force of the gripping fingers 98 and sliding the sleeve 90 off the catheter body 11 and connector 28. The sleeve 90 may then be discarded.

The protective tunneling sleeve 90 may be made of polyurethane, silicone, polyvinyl chloride, polyethylene, polypropylene, thermoplastic elastomers, or other similar materials known in the art.

Figure 13:
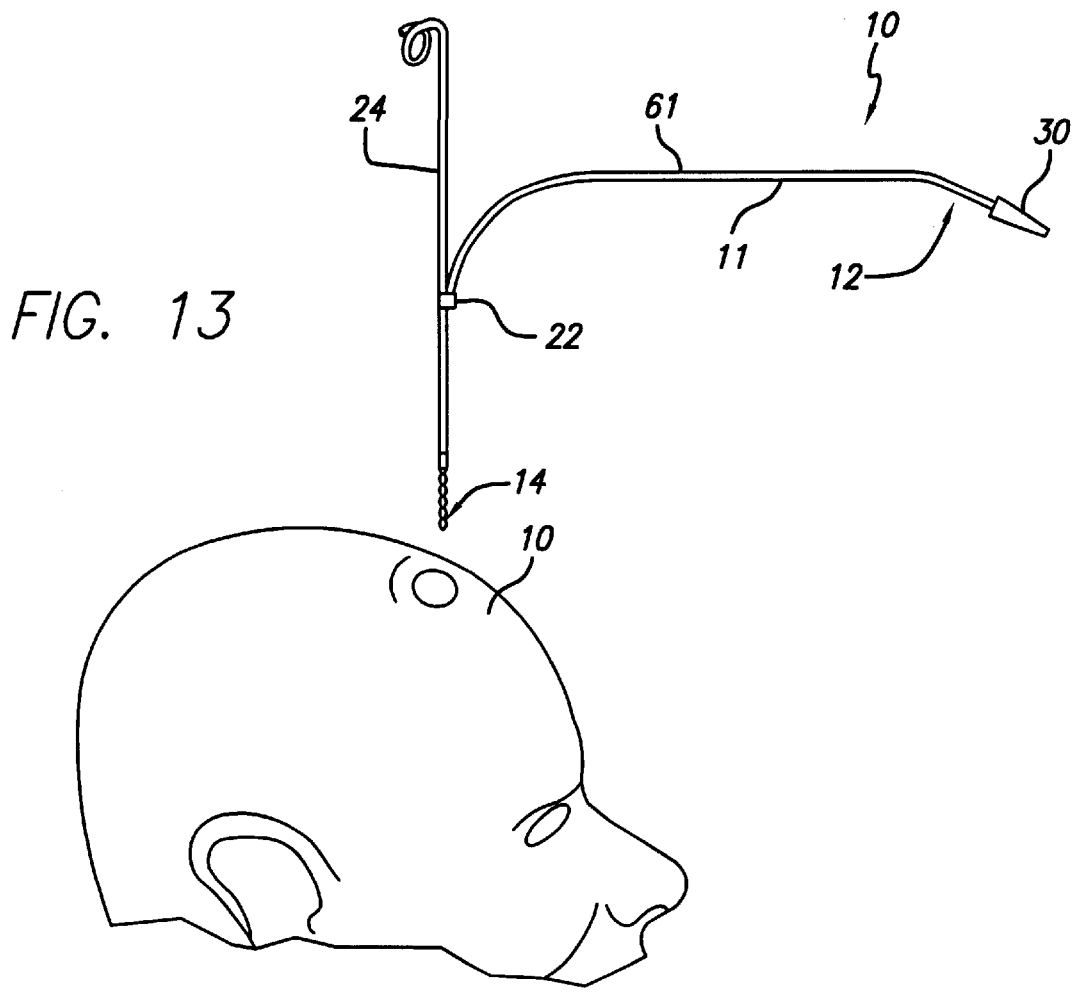
FIG. 13 is a view of a step of a method in accordance with aspects of the invention in which a catheter having a stylet inserted in the drainage/stylet port is being positioned above an access hole formed in the skull of a patient in preparation for insertion of the catheter into the ventricle, and further showing that the remainder of the catheter is unrestrained.

The preferred method of using the catheter 10 and devices previously shown and described is shown in FIGS. 13, 14, 15, 16, and 17. Referring now to FIG. 13 in more detail, an incision has been made in the scalp of the patient and an access hole 110 through the patient's skull has been formed. The access hole 110 may be made by means known to those skilled in the art, including a twist drill (not shown). The stylet 24 has been inserted through the drainage/stylet port 22 and into the drainage/stylet lumen 16 of the catheter to stiffen the distal end 14 of the catheter during insertion into the patient's ventricle. The catheter 10 will now be placed at a selected depth through the access hole and into the ventricle.

It should be noted that the proximal end of the catheter 12 is unrestrained at this time. It is free to move about as the physician is inserting the distal end 14 into the precisely correct position in the ventricle. This unrestrained proximal end provides a distinct advantage over prior devices in that it permits the physician much more freedom of movement when placing the catheter 10. It should also be noted that the protective tunneling sleeve is not present on the catheter at this time. The drainage/stylet port 22 must be open to receive stylet, thus the sleeve has been moved out of the way.

Figure 14:
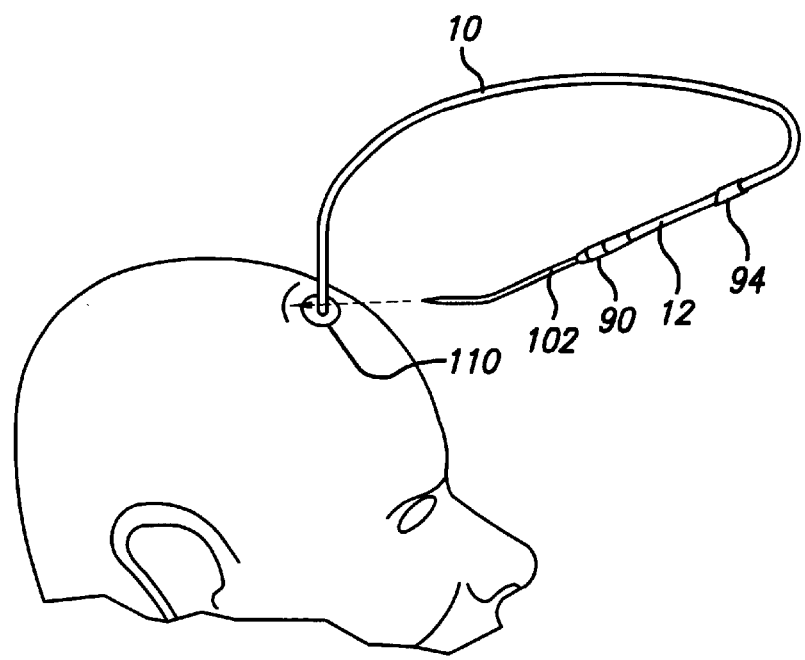
FIG. 14 is a view of another step of a method in accordance with aspects of the invention in which the distal end of the catheter has been properly positioned in the patient's ventricle and has been fixed into position for long-term use, the protective sheath and the solid trocar have been attached to the proximal end of the catheter and are shown in position for forming a subdermal tunnel.

In the embodiment shown in FIG. 14, the catheter 10 has been inserted in the patient's ventricle through the access hole 110 and the protective tunneling sleeve 90 has been mounted over the proximal end of the catheter. Although not shown to scale so that the illustration will be clearer, the drainage/stylet port 22 is not covered by the sleeve distal end 94. The solid trocar 102 barb 104 has been inserted in the tunneling opening 100 of the sleeve and the trocar is being moved toward the access hole 110 to begin the process of forming a subdermal tunnel adjacent the access hole 110.

Figure 15:
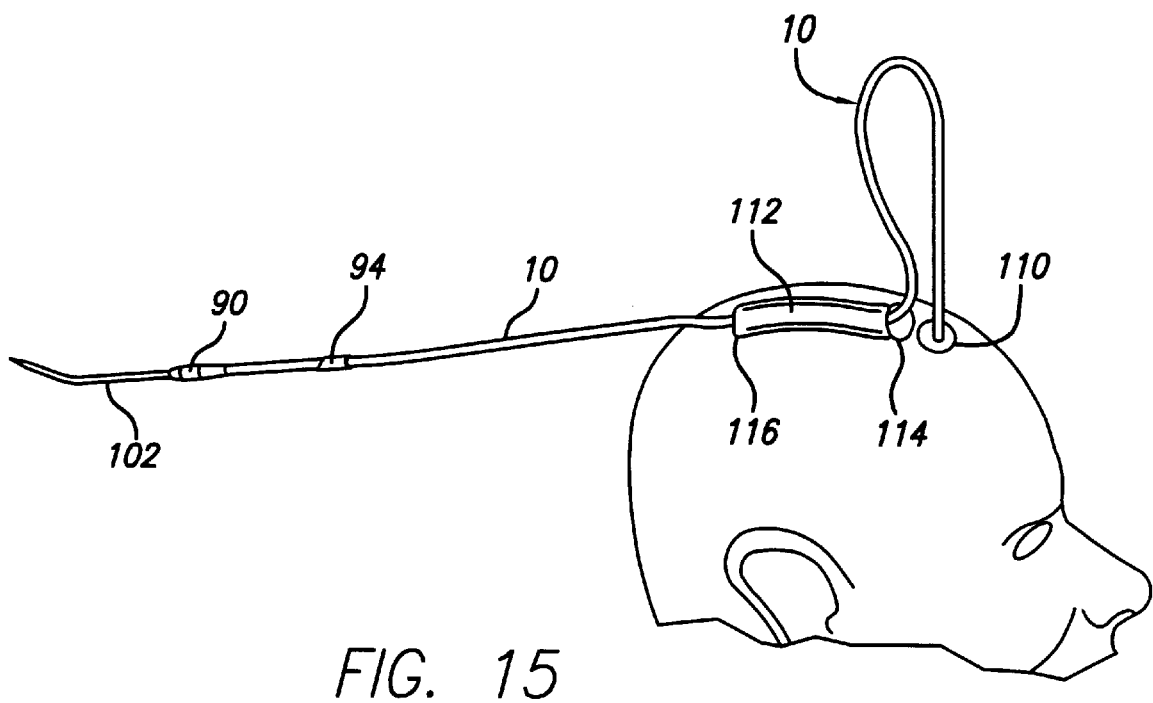
FIG. 15 presents a view of a step of a method in accordance with aspects of the invention in which the solid trocar has been used to form the subdermal tunnel in the patient's scalp, and has been drawn through the tunnel along with the proximal end of the catheter.

Referring now to FIG. 15, the trocar 102 has been advanced completely through the patient's scalp to form a subdermal tunnel 112 of approximately five centimeters. The trocar was started just adjacent the access hole 110 creating a tunnel entry opening 114 and was advanced away from the hole creating a tunnel exit opening 116. The catheter 10 is now being pulled taut in the tunnel 112. Because this tunneling process is away from the access hole, it is considered to be the traditional or forward tunneling technique. Tunneling away from the access hole has distinct advantages in that contaminants from the subdermal tunnel are not directed toward the access hole, which is open to the cranial vault, but are directed away from the hole 110. This greatly improves patient safety.

Because of the use of the miniaturized connector 28 on the proximal end of the catheter 10, it may be pulled through the tunnel by the tunneling instrument and the traditional tunneling technique may be used. As described above, each feature of the connector 28 was selected to result in a reduction in size so that the connector can be used in the traditional tunneling technique. A preferred diameter of the connector is 6 to 9 French with both the catheter diameter and the connector diameter being approximately the same.

Figure 16:
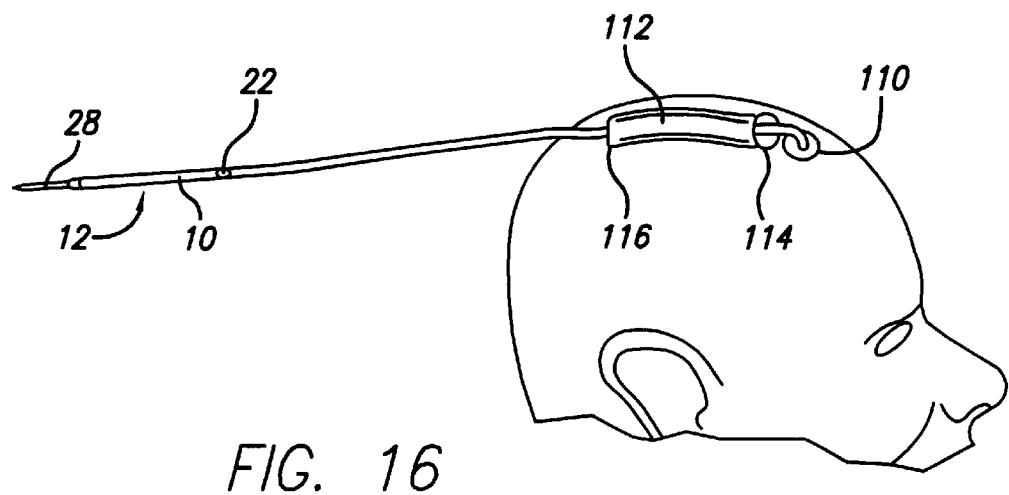
FIG. 16 presents yet another step of a method in accordance with aspects of the invention in which the solid trocar and the protective sheath have been removed from the proximal end of the catheter and the catheter has been pulled taut through the subdermal tunnel.
Figure 17:
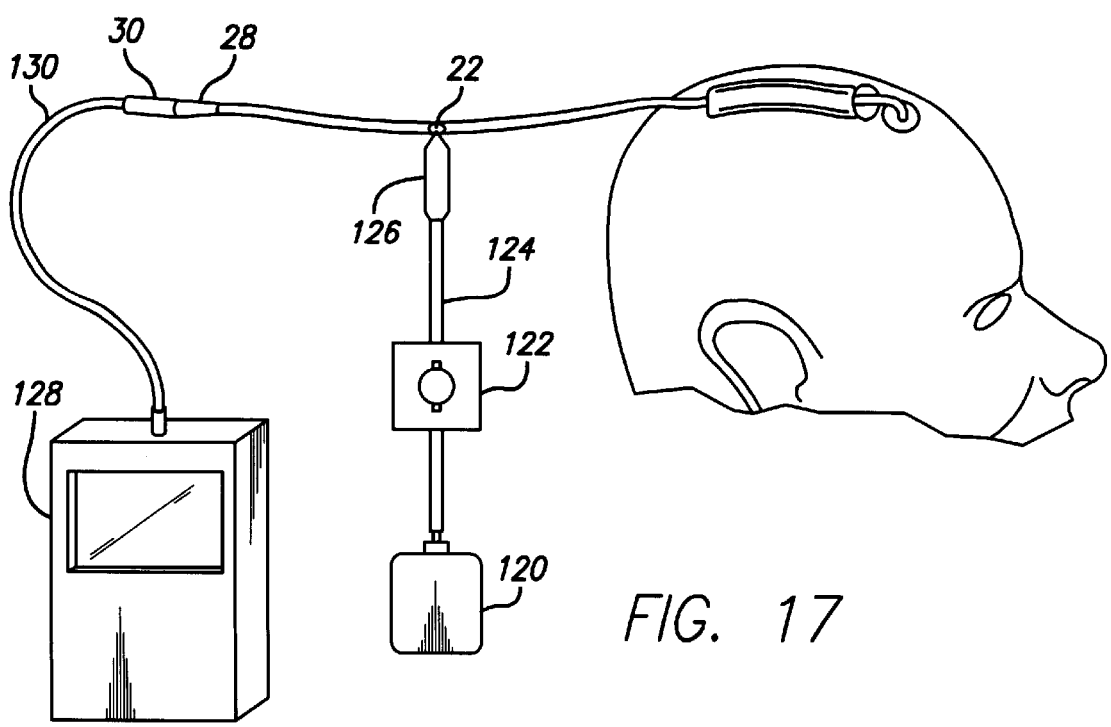
FIG. 17 presents yet another step of a method in accordance with aspects of the invention in which the scalp has been sutured over the properly positioned catheter, and the proximal end of the catheter has been connected to an intermediate cable which in turn has been connected to an instrument for analysis and display of pressure sensor signals, and a drainage bag has been connected to the drainage/stylet lumen of the catheter through use of a barbed connector located in the drainage/stylet port to drain CSF into the drainage bag.

Referring now to FIG. 16, the catheter 10 has been pulled taut within the tunnel, the tunneling instrument removed from the proximal end of the catheter and the protective tunneling sleeve has been removed from the catheter. The scalp located over the access hole 110, the entrance opening 114 and the exit opening 116 may now be sutured in place covering the catheter, as shown in FIG. 17. This approach not only provides resistance against the entry of pathogens and other infectious agents, but also is safer for the patient in that the catheter at the access hole is not exposed to forces that may cause it to be dislodged. The catheter is thus protected against attempted or inadvertent removal by a patient who is traumatized and who is moving his head, or who is irritated by the catheter and desires its removal, as sometimes happens with pediatric patients. It is also more aesthetically acceptable to relatives of the patient in that the catheter and the access hole are covered. This can provide a strong psychological advantage to the patient.

Referring further to FIG. 17, a fluid drainage apparatus 120, such as a flexible bag, to receive CSF is connected through a stopcock valve 122 by tubing 124 to a connector 126 that may be fitted to the drainage/stylet port 22 of the drainage/stylet lumen 16. The connector in this embodiment comprises a barb that is somewhat larger than the port 22 to that it fits tightly into the port to channel the fluid to the stopcock 122 and bag 120. Because the drainage/stylet lumen 16 is closed at a location just proximal to the port 22, the fluid will be directed through the barb connector 126.

Also in FIG. 17, a pressure monitoring apparatus and display 128 is connected to an intermediate cable 130 that includes on its distal end the female connector 30 described above. The female connector 30 is mated to the male connector 28 on the proximal end 12 of the signal conducting lumen 18, and thereby allows pressure sensor information to be conducted through the signal conducting lumen 18 to the pressure sensor monitor 128.

After completion of the surgical procedure, and connection of the catheter 10 to the pressure monitoring apparatus 128 and the drainage apparatus 124, the pressure monitor 128 will provide continuous monitoring of the intracranial pressure at the distal end 14 of the catheter 10. When it is determined that the intracranial pressure has risen to an undesirable level, CSF may be removed from the intracranial space by use of the stopcock 122 and fluid drainage apparatus 120.

Although a tunnel was made and the catheter 10 was directly pulled through the tunnel, other approaches may be used. For example, a working tunnel may initially be installed. In this case, the tunneling instrument 102 may be coupled to a hollow tunneling sheath (not shown) and the sheath pulled into the subdermal tunnel made by the instrument 102. After the tunneling sheath is in position in the tunnel made by the instrument 102, the instrument 102 is disconnected from the sheath while the sheath is in position. The sheath is then trimmed to a length of approximately one to two centimeters at each end beyond the end of the tunnel. The sheath then will keep the tunnel open so that various devices and instruments, including the miniature connector 28 may be threaded through it as needed. The male connector 28 would in this case also be smaller than the subdermal tunnel.

Figure 18:
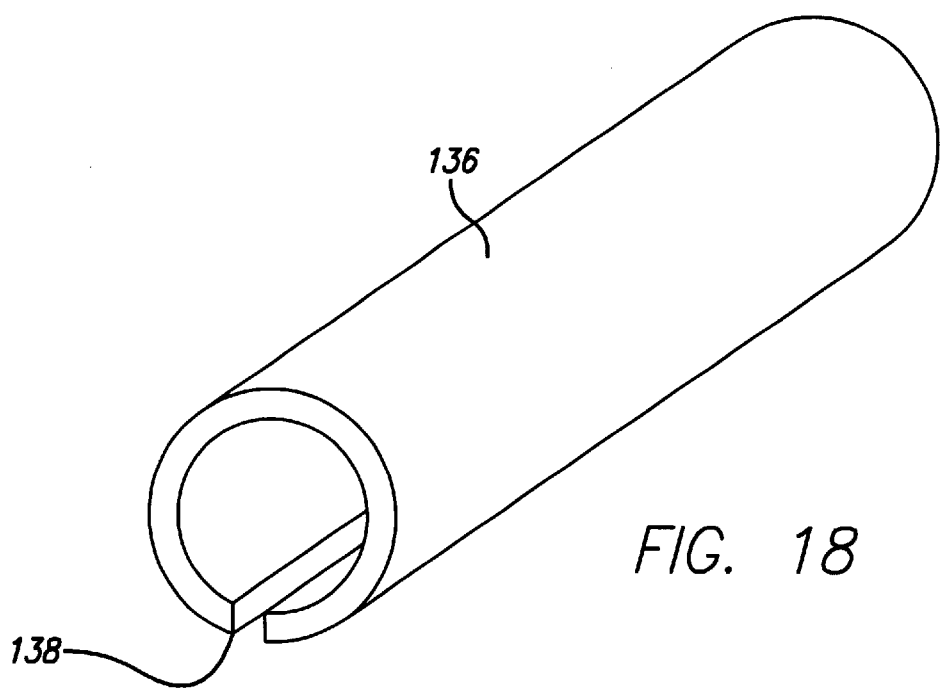
FIG. 18 presents an alternative drainage/stylet port protective sleeve usable on the catheter shaft to cover the drainage/stylet port and which can be slid along the shaft to uncover the drainage/stylet port, as desired.

Referring now to FIG. 18, an alternative drainage/stylet port 2 protection sleeve 136 is shown. This sleeve 136 is slotted 138 for ease in sliding the sleeve along the body of the catheter. The thickness of the sleeve and the width of the slot are selected to control the amount of pressure the sleeve 136 exerts against the body of the catheter and therefore the ease with which it may be slid. In such an embodiment, the protective tunneling sleeve 90 would not extend to the port 22 but would only cover the connector 28. In a preferred embodiment, the sleeve 136 was formed of PTFE, although other materials may be used. Having a slot 138 also permits complete removal of the sleeve, if desired. The sleeve 136 of this embodiment may be formed of PTFE, polyethylene, polypropylene, or other similar materials known in the art.

Although the drawings show an intracranial pressure sensor used at the distal tip of the catheter for sensing a biological parameter, and such is discussed in detail above, other types of sensors may be usable in such a catheter for sensing biological parameters. For example, a temperature sensor may be used, an oxygen measurement sensor may be used, and possibly others.

It should also be noted that the configuration of the catheter and the method of the invention permits drainage of fluid from the patient immediately upon positioning the catheter 10 in the ventricle. This drainage need not cease while the tunnel is being created because a traditional tunneling technique, i.e. away from the access hole, is used. This is especially true in the case where the slotted sleeve 136 of FIG. 18 is used. The sleeve 136 may be slid off the drainage/stylet port 22 until the last second before the port is pulled into the subdermal tunnel. This provides a distinct advantage to the patient in that an interruption in fluid drainage is kept to a minimum.

It will be appreciated that there has been provided a new and useful ventricular catheter and method of use that minimizes the possibility of contamination of the catheter or intracranial region by foreign matter or pathogens during surgical implantation of the catheter. The catheter disclosed above and illustrated in the drawings includes a sensor or sensors located at its distal end and is small enough so that it may be placed in a subdermal tunnel but need not be first located in the tunnel prior to location in the patient's cranium. The disclosed catheter can be tunneled in this way and is able to both measure a biological parameter or parameters within the cranium and provide for drainage of CSF when required, and has a small outer diameter for reduced trauma to the patient. Further, the catheter can accept a stylet for use in placing the catheter in the correct position in the cranium, yet provide means to protect the internal lumen or lumina of the catheter when exposed to the threading process through the tunnel. The catheter and method disclosed include a single catheter that may be used for immediately stabilizing the patient and is also usable for a long term, thereby obviating the need for two catheters and obviating the need for two access holes through the skull. Further, the disclosed method permits placing the catheter in the cranium of the patient first so that the patient may be stabilized as soon as possible, and then tunneling for more long term location of the catheter shaft in a subdermal location.

While only the presently preferred embodiments have been described in detail, as will be apparent to those skilled in the art, modifications and improvements may be made to the device disclosed herein without departing from the scope of the invention. Accordingly, it is not intended that the invention be limited, except as by the appended claims.

What is claimed is:

1. A method for accessing a site within the cranium of a patient, the method comprising the steps of:

forming an access hole through the skull;

introducing a catheter into the access hole, the catheter having a distal end and a proximal end with a sensor disposed at its distal end and a reduced diameter connector located at its proximal end, the reduced diameter connector adapted to conduct signals provided by the sensor;

positioning the distal end of the catheter at the cranial site; and thereafter forming a subdermal tunnel with an entrance at a location adjacent the access hole and an exit at a location remote from the access hole; and threading the proximal end of the catheter including the connector into the entrance of the subdermal tunnel and out the exit of the subdermal tunnel.

2. The method of claim 1 further comprising the steps of:
connecting the connector to a tunneling instrument prior to threading the catheter into the entrance, and wherein the step of forming the subdermal tunnel comprises the step of forming the tunnel with the tunneling instrument; and
disconnecting the connector from the tunneling instrument after the connector has been pulled out the exit.

3. The method of claim 1 further comprising the step of covering a drainage port formed in the catheter prior to the step of threading the catheter into the entrance.

4. The method of claim 3 further comprising the step of positioning a slotted sleeve over the drainage port to cover the port.

5. The method of claim 4 further comprising the step of sliding the slotted sleeve to cover and uncover the drainage port.

6. The method of claim 2 further comprising the steps of:
mounting a protective tunneling sleeve over the connector;
connecting the tunneling sleeve to the tunneling instrument;
threading the connector and the tunneling sleeve with the tunneling instrument;
disconnecting the tunneling sleeve from the tunneling instrument after the connector has been pulled through the tunnel by the tunneling instrument.

7. The method of claim 6 further comprising the step of covering a drainage port formed in the catheter with the protective tunneling sleeve prior to the step of threading the catheter into the entrance.

8. The method of claim 2 further comprising the step of:
mounting a protective tunneling sleeve over the connector, the tunneling sleeve having a diameter greater than the connector and greater than the tunneling instrument;
connecting the tunneling sleeve to the tunneling instrument; and
threading the catheter through the tunnel and increasing the size of the tunnel by pulling the tunneling sleeve and connector through the tunnel with the tunneling instrument.

9. The method of claim 1 further comprising the step of mounting a protective tunneling sleeve over the connector prior to the step of threading the catheter through the tunnel.

10. The method of claim 9 further comprising the steps of forming the final configuration of the subdermal tunnel with the tunneling sleeve.

11. The method of claim 1 further comprising the step of connecting a drainage lumen of the catheter to a fluid reservoir to drain fluid from the cranial site.

12. The method of claim 11 wherein the step of connecting a drainage lumen of the catheter to a fluid reservoir to drain fluid from the cranial site comprises connecting the drainage lumen prior to the step of threading the catheter through the tunnel.

13. The method of claim 11 wherein the step of connecting a drainage lumen of the catheter to a fluid reservoir to drain fluid from the cranial site comprises connecting the drainage lumen after the step of threading the catheter through the tunnel.

14. The method of claim 1 further comprising the step of connecting the connector to a monitor to display signals from the sensor after the step of threading the connector out the exit of the tunnel.

15. The method of claim 1 wherein the step of forming a subdermal tunnel comprises the step of forming a subdermal tunnel with a diameter no greater than 12 French.

16. The method of claim 1 wherein the step of forming a subdermal tunnel comprises the step of forming a subdermal tunnel with a diameter within the range of 6 to 9 French.

17. The method of claim 1 further comprising the step of conducting optical signals through the catheter from the sensor to the connector.

18. The method of claim 17 further comprising the step of connecting the optical signals at the catheter connector with an optical conductor in a complementary connector when the catheter connector and the complementary connector are joined together.

19. The method of claim 1 further comprising the step of conducting electrical signals through the catheter from the sensor to the connector.

20. The method of claim 19 further comprising the step of connecting the electrical signals at the catheter connector with an electrical conductor in a complementary connector when the catheter connector and the complementary connector are joined together.

21. The method of claim 1 wherein the step of positioning the distal end of the catheter at the cranial site comprises the step of inserting a stylet into the catheter to stiffen the catheter as it is positioned.

22. The method of claim 1 wherein the step of introducing a catheter having a reduced diameter connector located at its proximal end comprises introducing a catheter having a connector adapted to fit within a complementary connector, wherein the complementary connector is larger than the catheter connector and the tunnel and is connected to the catheter connector after the step of threading the catheter connector out the exit of the tunnel.

23. The method of claim 22 further comprising the steps of:
connecting the catheter connector to the complementary connector outside the tunnel; and
connecting the complementary connector to a monitor to display signals from the sensor.

24. The method of claim 23 further comprising the step of connecting a drainage lumen of the catheter to a fluid reservoir to drain fluid from the cranial site.

25. The method of claim 22 wherein the step of introducing a catheter having a connector adapted to fit within a complementary connector comprises the step of introducing the catheter with a male connector adapted to fit within a female complementary connector, wherein the female connector is larger than the catheter connector and the tunnel and is connected to the male catheter connector after the step of threading the male catheter connector out the exit of the tunnel.

26. The method of claim 25 further comprising the steps of:
connecting the male catheter connector to the female complementary connector outside the tunnel; and
connecting the female complementary connector to a monitor to display signals from the sensor.

27. The method of claim 23 further comprising the step of connecting a drainage lumen of the catheter to a fluid reservoir to drain fluid from the cranial site.

28. A method for accessing a site within the cranium of a patient, the method comprising the steps of:
forming an access hole through the skull;
introducing a catheter into the access hole, the catheter having a distal end and a proximal end with a sensor disposed at its distal end and a reduced diameter catheter connector located at its proximal end, the reduced diameter catheter connector adapted to conduct signals provided by the sensor;

positioning the sensor of the catheter at the cranial site;

forming a subdermal tunnel with an entrance at a location adjacent the access hole and an exit at a location remote from the access hole;

threading the catheter connector into the entrance of the subdermal tunnel and out the exit of the subdermal tunnel.

29. The method of claim 28 further comprising the steps of:

connecting the connector to a tunneling instrument prior to threading the catheter connector into the entrance, and wherein the step of forming the subdermal tunnel comprises the step of forming the tunnel with the tunneling instrument.

30. The method of claim 28 further comprising the step of mounting a protective tunneling sleeve over the catheter connector prior to the step of threading the catheter through the tunnel.

31. The method of claim 28 further comprising the steps of:

mounting a protective tunneling sleeve over the catheter connector;

connecting the tunneling sleeve to a tunneling instrument;

threading the catheter connector and the tunneling sleeve with the tunneling instrument;

disconnecting the tunneling sleeve from the tunneling instrument after the connector has been pulled through the tunnel by the tunneling instrument.

32. The method of claim 28 further comprising the step of covering a drainage port formed in the catheter prior to the step of threading the catheter into the entrance.

33. The method of claim 32 further comprising the step of positioning a slotted sleeve over the drainage port to cover the port.

34. The method of claim 28 further comprising the step of connecting a drainage lumen of the catheter to a fluid reservoir to drain fluid from the cranial site.

35. The method of claim 34 wherein the step of connecting a drainage lumen of the catheter to a fluid reservoir to drain fluid from the cranial site comprises connecting the drainage lumen prior to the step of threading the catheter through the tunnel.

36. The method of claim 34 wherein the step of connecting a drainage lumen of the catheter to a fluid reservoir to drain fluid from the cranial site comprises connecting the drainage lumen after the step of threading the catheter through the tunnel.

37. The method of claim 28 further comprising the step of connecting the catheter connector to a monitor to display signals from the sensor after the step of threading the connector out the exit of the tunnel.

38. The method of claim 28 further comprising the step of conducting optical signals through the catheter from the sensor to the catheter connector.

39. The method of claim 38 further comprising the step of connecting the optical signals at the catheter connector with an optical conductor in a complementary connector when the catheter connector and the complementary connector are joined together.

40. The method of claim 28 further comprising the step of conducting electrical signals through the catheter from the sensor to the connector.

41. The method of claim 40 further comprising the step of connecting the electrical signals at the catheter connector with an electrical conductor in a complementary connector when the catheter connector and the complementary connector are joined together.

42. The method of claim 28 wherein the step of positioning the distal end of the catheter at the cranial site comprises the step of inserting a stylet into the catheter to stiffen the catheter as it is positioned.

43. The method of claim 40 further comprising the steps of:

positioning a working sheath in the subdermal tunnel prior to threading the catheter through the tunnel; and threading the catheter through the sheath; and threading the catheter connector into the working sheath at the entrance of the subdermal tunnel and out the working sheath at the exit of the subdermal tunnel.

44. A method for accessing a site within the cranium of a patient, the method comprising the steps of:

forming an access hole through the skull;

introducing a catheter into the access hole, the catheter having a distal end and a proximal end with a sensor disposed at its distal end and a reduced diameter catheter connector located at its proximal end, the reduced diameter catheter connector adapted to conduct signals provided by the sensor;

inserting a stylet into the catheter to stiffen the catheter;

positioning the sensor of the catheter at the cranial site;

connecting the connector to a tunneling instrument;

forming a subdermal tunnel with a tunneling instrument with an entrance at a location adjacent the access hole and an exit at a location remote from the access hole;

threading the catheter connector into the entrance of the subdermal tunnel and out the exit of the subdermal tunnel;

connecting a drainage lumen of the catheter to a fluid reservoir to drain fluid from the cranial site.

* * * * *

UNITED STATES PATENT AND TRADEMARK OFFICE
CERTIFICATE OF CORRECTION

PATENT NO. : 6,453,185 B1
DATED : September 17, 2002
INVENTOR(S) : Jonathan B. O'Keefe It is certified that error appears in the above-identified patent and that said Letters Patent is hereby corrected as shown below:

Title page,
Item [54], change the title to read -- METHOD FOR ACCESSING A SITE WITHIN THE CRANIUM OF APATIENT --.

Item [56], U.S. PATENT DOCUMENTS, add the following:
-- 3,669,094   6/1972    Heyer, .
   4,114,603   9/1978    Wilkinson,
   4,723,556   2/1988    Sussman,
   5,117,836   6/1992    Miller,
   5,133,032   7/1992    Salter et al.,
   5,159,654   10/1992   Salter,
   5,191,898   3/1993    Millar,
   5,352,207   10/1994   Nussbaum --.

Signed and Sealed this

Thirty-first Day of December, 2002

JAMES E. ROGAN
*Director of the United States Patent and Trademark Office*